(12) United States Patent
Clark et al.

(10) Patent No.: US 10,613,065 B2
(45) Date of Patent: Apr. 7, 2020

(54) DETECTOR INLET AND SAMPLING METHOD

(71) Applicants: Alastair Clark, Watford (GB); Bruce Grant, Watford (GB); Matthew Easton, Watford (GB); Frederic Fournier, Watford (GB)

(72) Inventors: Alastair Clark, Watford (GB); Bruce Grant, Watford (GB); Matthew Easton, Watford (GB); Frederic Fournier, Watford (GB)

(73) Assignee: SMTIHS DETECTION-WATFORD LIMITED, Watford, Hertfordshire (GB)

( * ) Notice: Subject to any disclaimer, the term of this patent is extended or adjusted under 35 U.S.C. 154(b) by 169 days.

(21) Appl. No.: 15/129,525

(22) PCT Filed: Mar. 24, 2015

(86) PCT No.: PCT/GB2015/050870
§ 371 (c)(1),
(2) Date: Sep. 27, 2016

(87) PCT Pub. No.: WO2015/145132
PCT Pub. Date: Oct. 1, 2015

(65) Prior Publication Data
US 2017/0108480 A1    Apr. 20, 2017

(30) Foreign Application Priority Data

Mar. 27, 2014 (GB) .................................. 1405561.0

(51) Int. Cl.
*G01N 33/00* (2006.01)
*G01N 1/22* (2006.01)
*G01N 1/24* (2006.01)

(52) U.S. Cl.
CPC ....... *G01N 33/0011* (2013.01); *G01N 1/2202* (2013.01); *G01N 1/2273* (2013.01); *G01N 2001/245* (2013.01)

(58) Field of Classification Search
CPC ..................... G01N 33/0011; G01N 33/0009
(Continued)

(56) References Cited

U.S. PATENT DOCUMENTS 3,933,047 A    1/1976 Fowler
4,170,455 A *  10/1979 Henrie .................. G01N 25/32
                                              422/83
(Continued)

FOREIGN PATENT DOCUMENTS

CA       1036387 A      8/1978
CN    101135627 A      3/2008
(Continued)

OTHER PUBLICATIONS

Berrouk et al. ("Stochastic modelling of aerosol deposition for LES of 90 bend turbulent flow" International Journal of Heat and Fluid Flow 29 (Apr. 2008) 1010-1028).*

(Continued)

*Primary Examiner* — Nimeshkumar D Patel
*Assistant Examiner* — Jean F Morello
(74) *Attorney, Agent, or Firm* — Kevin E. West; Advent, LLP

(57) ABSTRACT

A detector comprising an analytical apparatus for detecting a substance of interest, and a detector inlet. The detector inlet comprises a flow passage for carrying a flow of fluid, the flow passage comprising a sampling volume, and a sampling inlet adapted to collect samples of the fluid from the sampling volume as the fluid flows past the sampling inlet, and to provide the samples to the analytical apparatus, wherein the flow of fluid carries particulates. The detector (Continued)

inlet also comprises a flow director arranged to vary a spatial distribution of the particulates carried by the fluid to increase a relative proportion of the particulates carried past the sampling inlet along the flow passage without entering the sampling volume.

20 Claims, 7 Drawing Sheets

(58) Field of Classification Search
USPC .......................................................... 73/23.37
See application file for complete search history.

(56) References Cited

U.S. PATENT DOCUMENTS

| | | | |
|---|---|---|---|
| 4,481,833 A | 11/1984 | Bajek | |
| 6,465,776 B1 | 10/2002 | Moini et al. | |
| 2003/0160174 A1* | 8/2003 | Grant | G01N 1/2258 250/339.13 |
| 2009/0026761 A1* | 1/2009 | McMillan | F16L 43/00 285/179 |
| 2012/0105839 A1 | 5/2012 | Novosselov et al. | |
| 2014/0041463 A1 | 2/2014 | Vethe et al. | |

FOREIGN PATENT DOCUMENTS

| | | |
|---|---|---|
| CN | 103534438 A | 1/2014 |
| DE | 4438267 A1 | 5/1996 |
| EP | 1868172 A2 | 12/2007 |
| JP | H07-260740 A | 10/1995 |
| JP | H08-28323 A | 1/1996 |
| JP | H08-285832 A | 11/1996 |
| JP | H09-311097 A | 2/1997 |
| JP | H09-311128 A | 12/1997 |
| JP | 2000249631 A | 9/2000 |
| JP | 2002243598 A | 8/2002 |
| RU | 2465964 C2 | 11/2012 |
| WO | 2009061863 A2 | 5/2009 |
| WO | 2011106840 A1 | 9/2011 |
| WO | 2013175947 A1 | 11/2013 |

OTHER PUBLICATIONS

English translation of Shiromaru (JP 09311097) specification, refernce dated Feb. 12, 1997.*
Combined Search and Examination Report for Great Britain Application No. GB1504963.8, dated Jan. 12, 2016.
Search Report for Great Britain Application No. GB1504963.8, dated Jan. 13, 2017.
Office Action for Chinese Application No. 201580028167.1, dated Aug. 28, 2018.
Akilli, H. et al., "Gas-solid flow behaviour in a horizontal pipe after a 908 vertical-to-horizontal elbow", Pwder Technology 116 (2001) 43-52.
Chong, Wong et al., "Experimental and computational modelling of solid particle erosion in a pipe annular cavity", Wear 303 (2013) 109-129.
Golomb, Richard et al., "A New Tailpipe Design for GE Frame-Type Gas turbines to Substantially Lower Pressure Losses", Proceedings of ASME Turbo Expo 2002, Jun. 3-6, 2002, Amsterdam, The Netherlands GT-2002-30149, 1-9.
Search Report dated Oct. 14, 2014 for Appln. No. GB1405561.0.
International Search Report dated Jul. 21, 2015 for PCT/GB2015/050870.
Combined Search and Examination Report for Application No. GB1805813.1, dated Oct. 26, 2018.
Office Action for Russian Application No. 2016139341/04(062762), dated Oct. 23, 2018.
Office Action for Japanese Patent Application No. 2017-501513, dated Jan. 29, 2019.
Chinese Office Action dated Sep. 18, 2019 for Appln. No. 201580028167.1.
Japanese Office Action dated Oct. 1, 2019 for Appln. No. 2017-501513.
Russian Office Action dated Aug. 12, 2019 for Appln. No. 2016139341/04 (062762).

* cited by examiner

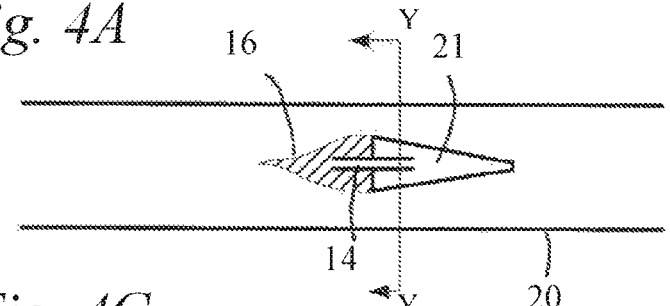
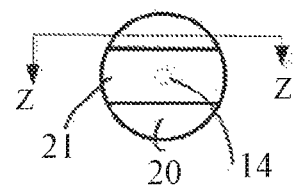
Fig. 4A
Fig. 4B
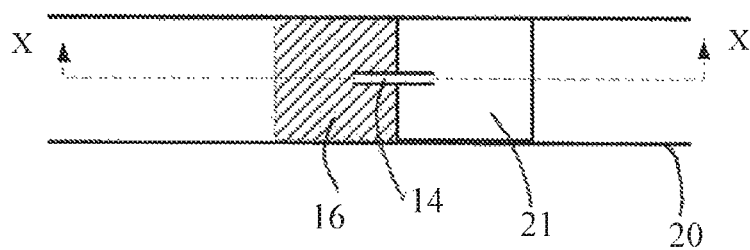
Fig. 4C
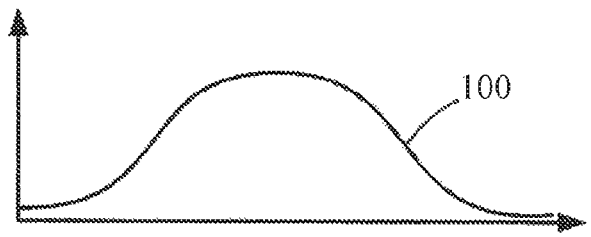
Fig. 4D
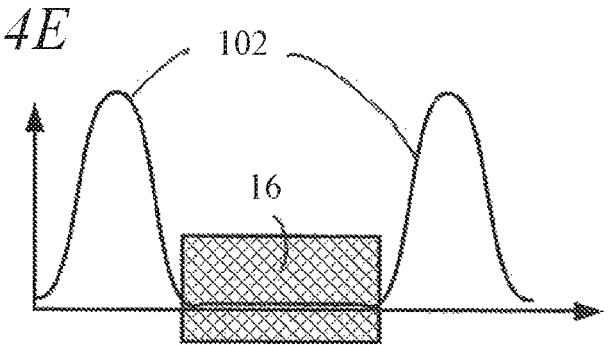
Fig. 4E

DETECTOR INLET AND SAMPLING METHOD

The present disclosure relates to detection methods and apparatus, and more particularly to methods and apparatus for obtaining samples for detectors, still more particularly to methods and apparatus for obtaining samples of vapours in the presence of particulates, these methods and apparatus may find particular application in spectrometry, for example ion mobility spectrometry and mass spectrometry.

Some detectors operate by "inhaling" a stream of fluid, such as air, into a detector inlet and sampling that air with an analytical apparatus to detect substances of interest. That inhaled stream of air can be sampled from the detector inlet using a sampling inlet such as a pinhole, capillary or membrane inlet.

Often, hand held, or portable devices may be needed for example for use by military and security personnel. These personnel frequently operate in hostile environments in the presence of large quantities of dust and grit and other particulate matter. Such particulates may obstruct the sampling inlet, or otherwise damage the detector. In some cases, particulates carried by the stream of air may comprise substances to which the detector is sensitive. If these accumulate in a detector or its inlets they may contaminate the detector, and may cause recovery time issues.

Embodiments of the disclosure will now be discussed, by way of example only, with reference to the accompanying drawings, in which:

FIGS. 4A, 4B and 4C show schematic views of a detector inlet;

FIG. 4D and FIG. 4E illustrate a spatial distribution of particulates across the flow passage in the detector inlet of FIG. 4;

In the drawings like reference numerals are used to indicate like elements.

Figure 1:
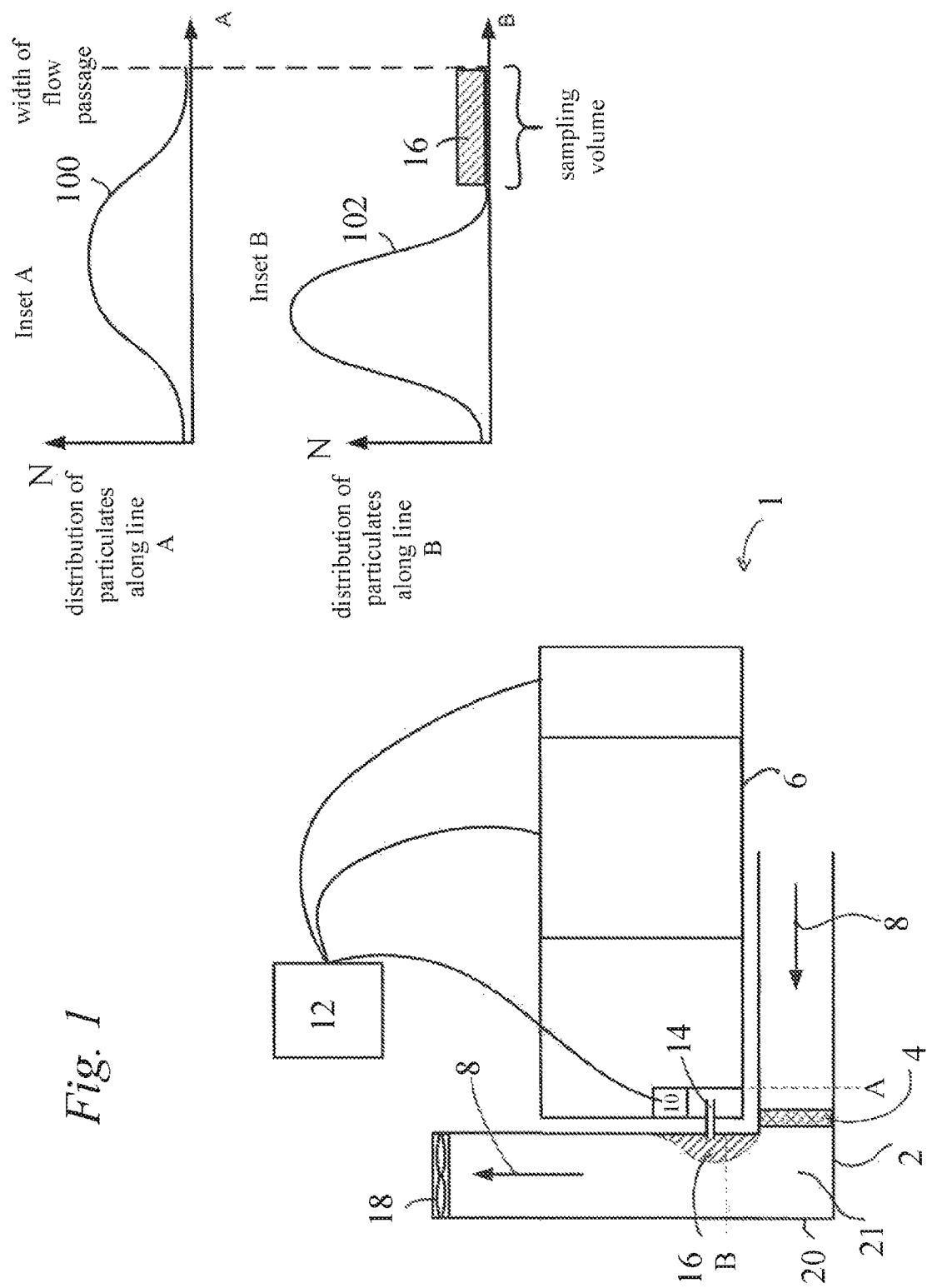
FIG. 1 shows an example of a detector with a detector inlet.

Embodiments of the disclosure relate to detectors for detecting substances of interest, and to detector inlets arranged to obtain samples for analysis in the detectors.

To obtain a sample, a fluid can be inhaled into a detector inlet and flowed to an outlet along a flow passage. A sampling inlet is coupled to the flow passage to provide samples of the fluid to an analytical apparatus. Where particulates are present in the environment they are carried by the inhaled flow, and are spatially distributed throughout it. Embodiments of the disclosure aim to direct the flow of fluid with a flow director that varies this spatial distribution of particulates. This provides a volume of the flow passage, downstream of the flow director, in which the spatial distribution of particulates is depleted. The sampling inlet can be arranged to obtain samples from this depleted sampling volume to reduce the risk of contaminating the detector with unwanted particulate material, or simply blocking the sampling inlet.

This modification of the distribution of particulates may be achieved, for example, by speeding up, slowing down, or changing the direction of at least a part of the fluid flow along the flow passage.

FIG. 1 shows a detector 1 comprising a detector inlet 2, coupled to an analytical apparatus 6 by a sampling inlet 14, such as a pinhole, capillary or membrane inlet, and a sampler 10 arranged to obtain samples of the fluid via the sampling inlet 14 from a sampling volume 16 around the sampling inlet 14.

The detector inlet 2 shown in FIG. 1 comprises a flow passage for carrying a flow of fluid 8 past the sampling inlet 14. As illustrated the detector inlet 2 of FIG. 1 comprises a flow provider 18 arranged to flow the fluid into the flow passage, past the sampling inlet 14, and along the flow passage 20 to an outlet. The detector inlet 2 may also comprise a heater 4 which may be arranged to heat the flow of fluid 8 upstream of the sampling inlet 14.

The flow passage 20 comprises a flow director 21 which, in the example of FIG. 1, is provided by a bend in the flow passage 20 arranged to change the direction of the fluid flow upstream from the sampling inlet 14.

The sampling inlet can be coupled to the flow passage 20 and adapted for collecting samples of the fluid from a sampling volume 16 in the flow passage 20 around the sampling inlet 14. The sampler 10 is configured to draw a selected volume of fluid, smaller than the sampling volume 16, through the inlet to provide a sample to the analytical apparatus. The sampler 10 may comprise an electromechanical actuator, for example a solenoid driven actuator, and/or a mechanical pump arranged to transfer vapour from the sampling volume 16, through the sampling inlet 14 and into the analytical apparatus.

The analytical apparatus 6 shown in FIG. 1 comprises a mass spectrometer. A mass spectrometer may comprise an ioniser, an ion accelerator, a beam focusser, a magnet, and a faraday collector arranged to perform mass spectrometry analysis on samples of vapour. As illustrated, a controller 12 is coupled to control the analytical apparatus, the flow provider, the heater, and the sampler. The controller 12 may comprise a processor and a memory storing instructions for operation of the detector 1.

In operation of the embodiment illustrated in FIG. 1, the flow provider 18 flows fluid along the flow passage, and the bend in the flow passage 20 changes the direction of the fluid flow upstream from the sampling inlet 14. By directing the flow in this way, the spatial distribution of particulates across the fluid flow can be changed to increase a proportion of the particulates which flow past the sampling inlet 14 without entering a volume around the sampling inlet 14. In the example shown in FIG. 1 this occurs because the inlet is arranged on the inside of the bend, and particulates carried by the flow tend to flow along the outside of the bend, away from the sampling inlet 14. This change in distribution is illustrated in Inset A of FIG. 1. Inset A illustrates a plot 100 of a spatial distribution of particulates along the line A, the horizontal axis indicates position across the direction of flow of the fluid. The plot 100 shown in Inset A of FIG. 1 corresponds to a spatial distribution of particulates upstream from the flow director 21. Inset B illustrates a plot 102 of a spatial distribution of particulates along the line B, across the direction of flow of the fluid in the region of the sampling volume 16. From a comparison of Inset A and Inset B, it can be seen that the spatial distribution of particulates across the flow of fluid 8 is changed to increase the relative proportion of the particulates carried past the sampling inlet 14 along the flow passage 20 without entering the sampling volume 16.

The controller 12 can control the sampler 10 to draw a sample from the sampling volume 16 and to provide the sample to the analytical apparatus 6. The analytical apparatus 6 illustrated in FIG. 1 can then analyse the sample by performing mass spectrometry on the sample.

As will be appreciated, the detector inlet 2 of the present disclosure may also be used in other kinds of detectors such as, detectors comprising ion mobility spectrometers, time of flight ion mobility spectrometers, chromatography apparatus and other kinds of analysers for detecting substances of interest.

Figure 2:
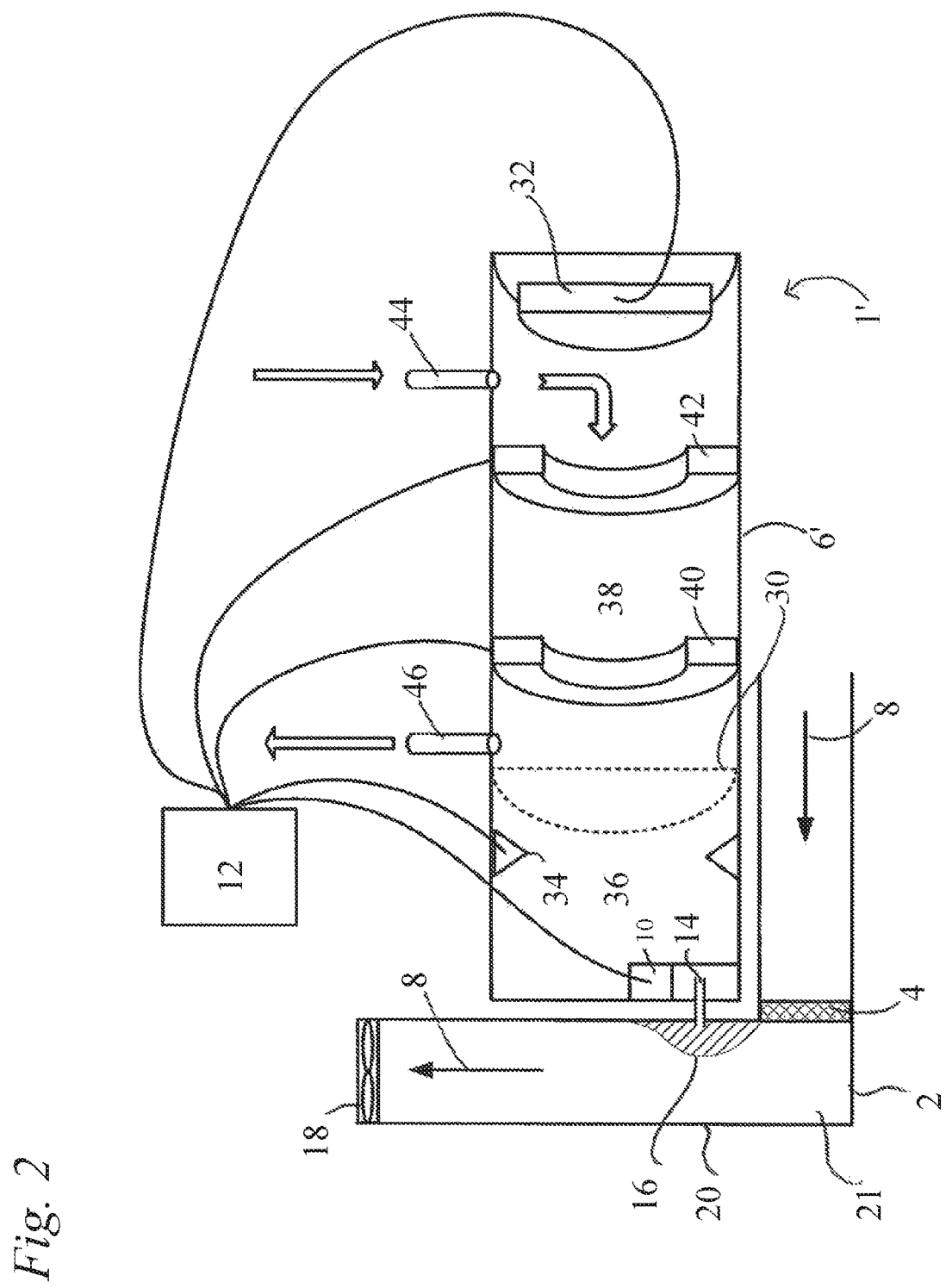
FIG. 2 shows another example of a detector with a detector inlet.

FIG. 2 shows a detector 1 in which the analytical apparatus comprises an ion mobility spectrometer 6' but which is otherwise identical to the apparatus shown in FIG. 1. The ion mobility spectrometer of FIG. 2 is coupled to a detector inlet 2 by a sampling inlet 14. A sampler 10 is arranged to obtain samples of the fluid through the sampling inlet 14 and to provide them to the ion mobility spectrometer 6'. As in the example of FIG. 1, the controller 12 may comprise a processor and a memory storing instructions for operation of the detector 1. Also as in FIG. 1, the sampler 10 may comprise an electromechanical actuator, for example a solenoid driven actuator, and/or a mechanical pump arranged to transfer vapour from the sampling volume 16 through the sampling inlet 14 into the analytical apparatus.

In FIG. 2, the ion mobility spectrometer 6' may comprise a reaction region 36 in which a sample can be ionised by an ioniser 34. The sampler 10 can be operated to obtain a sample from the sampling volume 16 through the sampling inlet 14, and to provide the sample to the reaction region 36. Some examples of sampling inlets 14 include 'pinhole' inlets, which may be approximately 0.7 mm in diameter, for example the diameter may be at least 0.4 mm, for example at least 0.6 mm, for example less than 1.0 mm, for example less than 0.8 mm.

A gate electrode 30 may separate the reaction region 36 from a drift chamber 38. The gate electrode 30 may comprise an assembly of at least two electrodes, which may be arranged to provide a Bradbury-Nielsen gate. The drift chamber 38 can comprise a collector 32 toward the opposite end of the drift chamber 38 from the gate electrode 30 for detecting ions. The drift chamber also comprises a drift gas inlet 44, and a drift gas outlet 46 arranged to provide a flow of drift gas along the drift chamber 38 from the ion collector 32 towards the gate 30. The sampler 10 can be operated by the controller 12 to obtain fluid from sampling volume 16 through the sampling inlet 14. The sampler 10 can also be operated to provide an obtained sample into the reaction region 36 of the spectrometer 6'. The reaction region shown in FIG. 2 comprises an ioniser 34 for ionising a sample. The ioniser 34 may comprise a corona discharge ioniser. The drift chamber 38 may comprise drift electrodes 40, 42 for applying an electric field along the drift chamber 38 to move ions towards the collector 32 against the flow of the drift gas. Although the apparatus of FIG. 2 is illustrated as comprising two drift electrodes 40, 42, some embodiments may comprise more than two drift electrodes.

In operation, the flow provider 18 can be operated to direct a flow of fluid 8 past the flow director 21 in the flow passage 20 and then past the sampling inlet 14. As the fluid flows past the flow director 21 the change in direction it provides varies the distribution of particulates transverse to the direction of flow of the fluid relative to the shape of said distribution upstream of that bend. This may provide a depleted region of the cross section of the flow passage 20 through which relatively few particulates flow, the majority of the particulates being carried through other parts of the cross section of the flow passage. This depleted region may persist for a distance along the flow passage 20 thereby defining a sampling volume 16 in which the number (e.g. count per unit volume) of particulates is relatively lower than in other regions of the flow passage.

The sampler 10 can be operated to obtain a sample of fluid from this sampling volume 16 via the sampling inlet 14. The obtained sample of fluid can then be provided to an analytical apparatus. In the example of FIG. 2 the analytical apparatus comprises an ion mobility spectrometer 6'.

As explained above, detector inlets of the present disclosure find particular application in portable devices which may be used in hostile environments where dust and contaminants are prevalent. These detector inlets may be used with a variety of analytical apparatus, such as the mass spectrometer of FIG. 1 and the ion mobility spectrometer of FIG. 2, other kinds of analysers, spectrometers and/or chromatography apparatus. In addition, the detector inlet 2 may have different configurations.

As shown in FIG. 3, FIG. 4, and FIG. 5, a detector inlet 2 may comprise flow directors having different structural forms. Each of these flow directors may vary the distribution of particulates in the flow of fluid 8 to provide a sampling volume 16 having a relatively lower concentration of particulates (e.g. a lower mass per unit volume, or particulate count per unit volume). In some embodiments the flow director 21 may provide a sampling volume 16 where fluid flow is slow compared to the flow of fluid 8 past the sampling volume 16 along the flow passage. This may be achieved by providing a region of slow flow, and/or by accelerating part of the flow.

Accelerating may comprise changing the direction of at least a part of the flow of fluid 8 or increasing its speed, or both. Providing a region of slow flow may comprise providing a culvert or recess or other sheltered region as in FIG. 5.

FIG. 3 shows an example of a detector inlet 2 comprising a flow director, a sampling inlet 14, and a flow passage. FIG. 3 comprises three views of the detector inlet 2, FIGS. 3A, 3B and 3C. FIG. 3A shows a section view of the detector inlet 2 from the line indicated as X-X in FIG. 3C. FIG. 3B shows a section view of the detector inlet 2 from the line indicated as Y-Y in FIG. 3A. FIG. 3C shows a section view of the detector inlet 2 from the line indicated as Z-Z in FIG. 3B.

As can be seen in FIG. 3A and FIG. 3B, in the embodiment illustrated in FIG. 3 the flow director 21 protrudes into the flow passage 20 from a wall of the flow passage. The flow director 21 can direct the flow of fluid to flow only to one side of the flow director. The flow director 21 may protrude further into the flow passage 20 toward the flow director's downstream end than towards its upstream end. For example, the flow director 21 may have a sloped surface, which may be straight, curved or graduated, to provide a ramp. As illustrated in FIG. 3A, the sampling inlet 14 may be disposed downstream of the flow director 21 to obtain samples from a sheltered sampling volume 16. The speed of the fluid flow in the sampling volume 16 may be lower than the speed of fluid flow past the sampling volume 16. The speed of the fluid flow past the sampling volume 16 may be higher than the speed of the fluid flow upstream from the flow director.

Figure 3A:
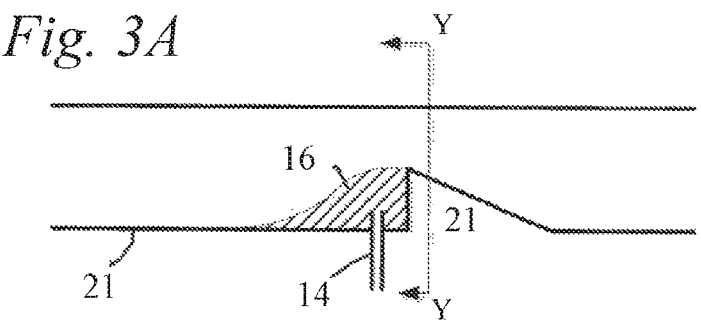
FIGS. 3A, 3B and 3C show schematic views of a detector inlet.
Figure 3B:
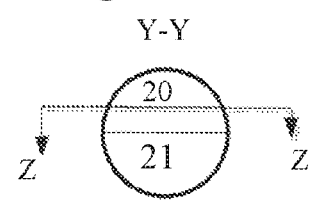
Figure 3C:
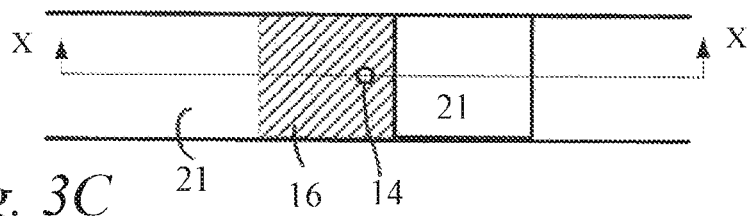
Figure 3D:
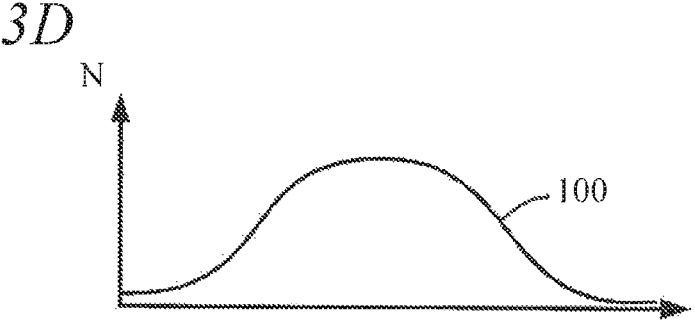
FIG. 3D and FIG. 3E illustrate a spatial distribution of particulates across the flow passage in the detector inlet of FIG. 3.
Figure 3E:
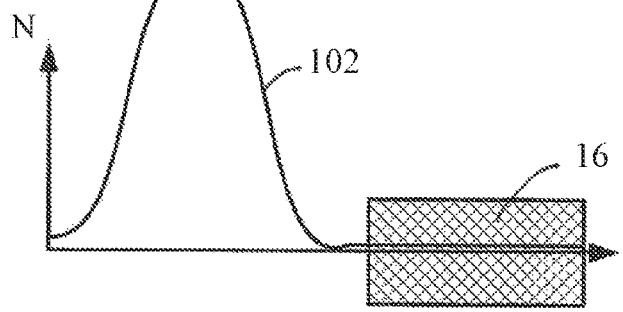
Figure 5A:
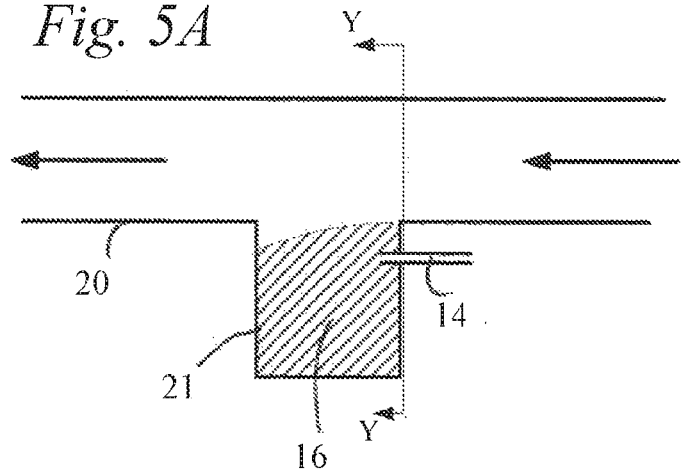
FIGS. 5A, 5B and 5C show schematic views of a detector inlet.
Figure 5B:
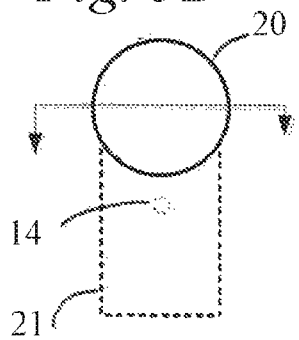
Figure 5C:
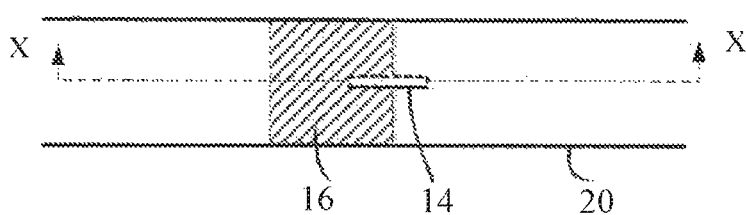
Figure 5D:
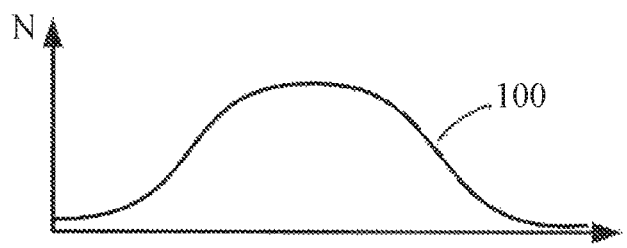
FIG. 5D and FIG. 5E illustrate a spatial distribution of particulates across the flow passage in the detector inlet of FIG. 5.
Figure 5E:
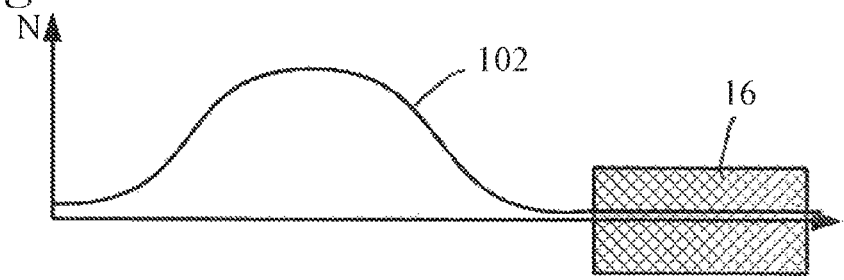

FIG. 3D illustrates one example of a spatial distribution of particulates across the flow passage 20 upstream from the flow director. As can be seen in FIG. 3D, upstream from the flow director, particulates carried by the fluid flow may be distributed relatively evenly across the width of the flow. As will be appreciated in the context of the present disclosure, the distribution shown in FIG. 3D is merely exemplary and may be different in different conditions, for example, gravity may skew the distribution in one direction or another depending on the orientation of the device. As illustrated in FIG. 3E, downstream from the flow director, the spatial distribution of particulates across the direction of flow of the fluid may be modified by the flow director. For example, as illustrated in FIG. 3E the spatial distribution of particulates may be more uneven downstream from the flow director 21 than upstream from it. As shown in FIG. 3E, downstream from the flow director the particulates are more concentrated outside the sampling volume than within it. As a result of this unevenness in the distribution, particulates may be more likely to flow past the inlet without entering the sampling volume 16.

FIG. 4 shows another example of a flow director. FIG. 4 comprises three views of a detector inlet 2, FIGS. 4A, 4B and 4C. FIG. 4A shows a section view of the detector inlet from the line indicated as X-X in FIG. 4C. FIG. 4B shows a section view of the detector inlet 2 from the line indicated as Y-Y in FIG. 4A. FIG. 4C shows a section view of the detector inlet 2 from the line indicated as Z-Z in FIG. 4B.

As can be seen from FIG. 4A and FIG. 4B, the flow director 21 may be arranged to separate the fluid flow into at least two separate flow paths, separated by the flow director. For example the flow director 21 of FIG. 3B may be arranged mid-flow, spanning across the flow passage, and coupled to two walls of the flow passage. The flow director 21 shown in FIG. 4B may be tapered so that it is narrower towards its upstream end than it is towards its downstream end. As shown in FIG. 4A and FIG. 4C, the flow director 21 provides a sheltered sampling volume 16 at its downstream end, and the sampling inlet 14 may be arranged on the downstream end of the flow director. The passage of fluid flow on both sides of this flow director 21 may reduce the tendency of particles to accumulate around the sampling inlet 14.

FIG. 4D illustrates one example of a spatial distribution of particulates across the flow passage 20 upstream from the flow director. The description of FIG. 3D, above, also applies to FIG. 4D. FIG. 4E illustrates a shape of a distribution of particulates across the direction of the fluid flow in the region of the sampling volume 16. It can be seen from FIG. 4E that the flow director 21 can increase the probability that particulates will flow around the sampling volume 16, rather than flowing through it.

FIG. 5 illustrates another example of a detector inlet. FIG. 5 comprises three views of a detector inlet, FIGS. 5A, 5B and 5C. FIG. 5A shows a section view of the detector inlet 2 from the line indicated as X-X in FIG. 5C. FIG. 5B shows a section view of the detector inlet 2 from the line indicated as Y-Y in FIG. 5A. FIG. 5C shows a section view of the detector inlet 2 from the line indicated as Z-Z in FIG. 5B.

In FIG. 5, the flow director 21 is provided by a variation in cross section of the flow passage. In this embodiment, the flow director 21 comprises a recess in a wall of the flow passage, and the sampling inlet 14 is arranged in the recess. For example, the sampling inlet 14 may be arranged in the upstream wall of the recess, so the flow can be directed away from the sampling inlet 14. Accordingly, the fluid flow can be directed past the recess (and the sampling volume), thereby reducing the probability that particulates carried by the flow of fluid will enter the sampling volume 16.

FIG. 5D illustrates one example of a spatial distribution of particulates across the flow passage 20 upstream from the flow director. The description of FIG. 3D, above, also applies to FIG. 5D. FIG. 5E illustrates the spatial distribution of particulates across the direction of the flow downstream of the flow director 21 where the flow passes the recess. FIG. 5E illustrates a lower number of particulates in the recess than in the fluid flowing past it, thereby illustrating one way in which the shape of the spatial distribution of particulates may be changed by a flow director. It can be seen in FIG. 5E that, where the flow director 21 comprises a recess, and in some other examples, total width and/or shape of the flow passage 20 may be changed by a flow director, so although part of the distribution of particulates may be relatively unchanged the shape of the distribution is still different from its shape upstream of the flow director.

FIG. 6A shows another example of a flow director. In the example of FIG. 6A the flow director 21 comprises a series of foils 50, 52, 54, 56, 58, 60, 62. The foils, 50-62, may be ring shaped and may be arranged on a common axis. Each foil 50-62, may have an aerofoil type profile, or be otherwise configured, for example by being shaped, profiled and/or angled, to funnel particulates inside the foils in preference to fluid. In an embodiment the foils 50-62 may be configured, for example by being shaped, profiled and/or angled, to preferentially direct fluid flow outside of the foils.

The foils 50-62 may be spaced apart in the direction of flow of the fluid. At the upstream end of this flow director 21, one of the foils 50 may span most or all of the width of the flow passage. The span of the downstream foils 52, 54, 56, 58, 60, 62 may become successively smaller, to provide a tapered structure. Each of the foils may be pitched (e.g. at an acute angle) relative to the direction of flow of the fluid along the flow passage 20. The foils may all have the same pitch, or the pitch may be varied. The foil 62 at the downstream end of the flow director may be smaller than the other foils. The sampling inlet 14 illustrated in FIG. 6 is arranged to obtain samples of fluid from a sampling volume 16 downstream from this last, most downstream, foil in the series of foils. The foils may be heated to inhibit the accumulation of substances on the foils, and/or to vapourise aerosols carried by the flow of air along the detector inlet.

Although they are described as being rings, the foils of course need not be circular rings and may be non-circular, for example oval, tapered, rectangular, square or any other shape. The foils may be arranged to be symmetrical about a common axis, for example an axis aligned with the direction of flow of fluid along the flow passage. For example, one or more of the foils may be helical, or all of the circular foils may be replaced by a single helical foil. For example a helical foil may spiral inward along the flow passage so that it has a greater diameter at its upstream end than at its downstream end.

FIG. 6B illustrates one example of a spatial distribution of particulates across the flow passage 20 upstream from the flow director foils 50-62 of FIG. 6A. The description of FIG. 3D, above, also applies to FIG. 6B. FIG. 6C illustrates the spatial distribution of particulates across the direction of the flow downstream of the flow director foils 50-62 where the flow passes the inlet 14. As shown in FIG. 6C, in this region, downstream from the foils 50-62, the particulates are concentrated into a narrow region of the flow passage.

Figure 6A:
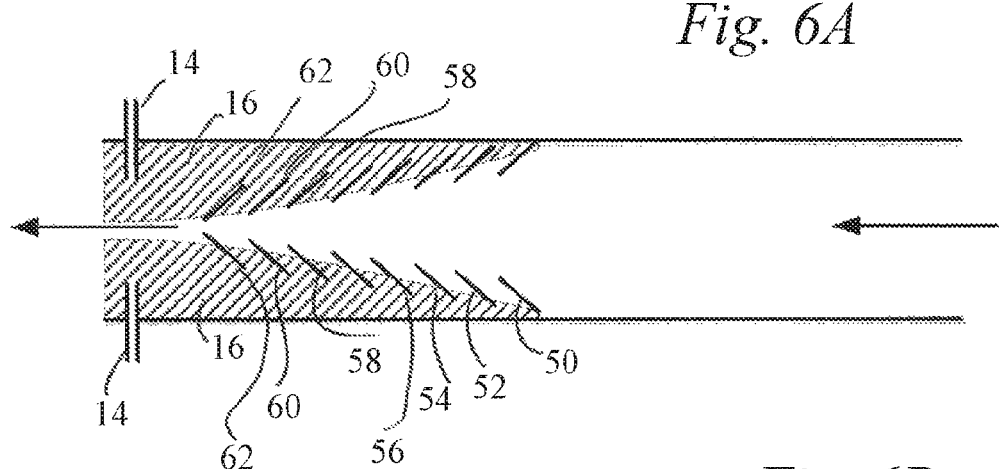
FIG. 6A shows a schematic representation of another detector inlet.
Figure 6B:
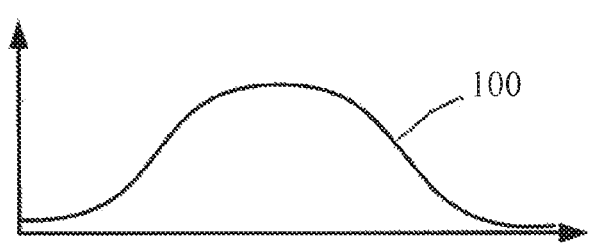
FIG. 6B and FIG. 6C illustrate a spatial distribution of particulates across the flow passage of the detector inlet of FIG. 6A.
Figure 6C:
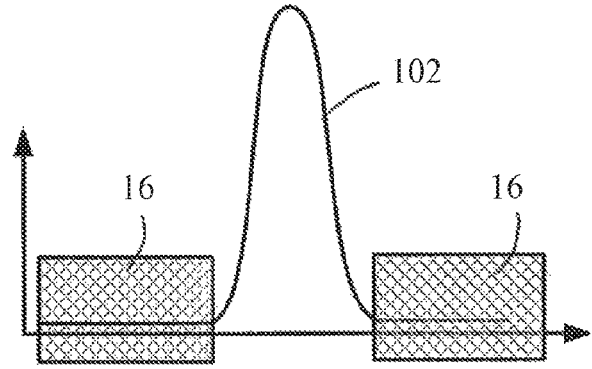

Some flow directors (e.g. for example those shown in FIG. 3, FIG. 4, and FIG. 6A) may provide a reduction in the cross section of the flow passage 20 through which the fluid can flow. In some embodiments, the flow director may cause a change in direction of the fluid flow which could cause undesirable concentration and/or deposition of particulates in a region of the flow passage.

Figure 7:
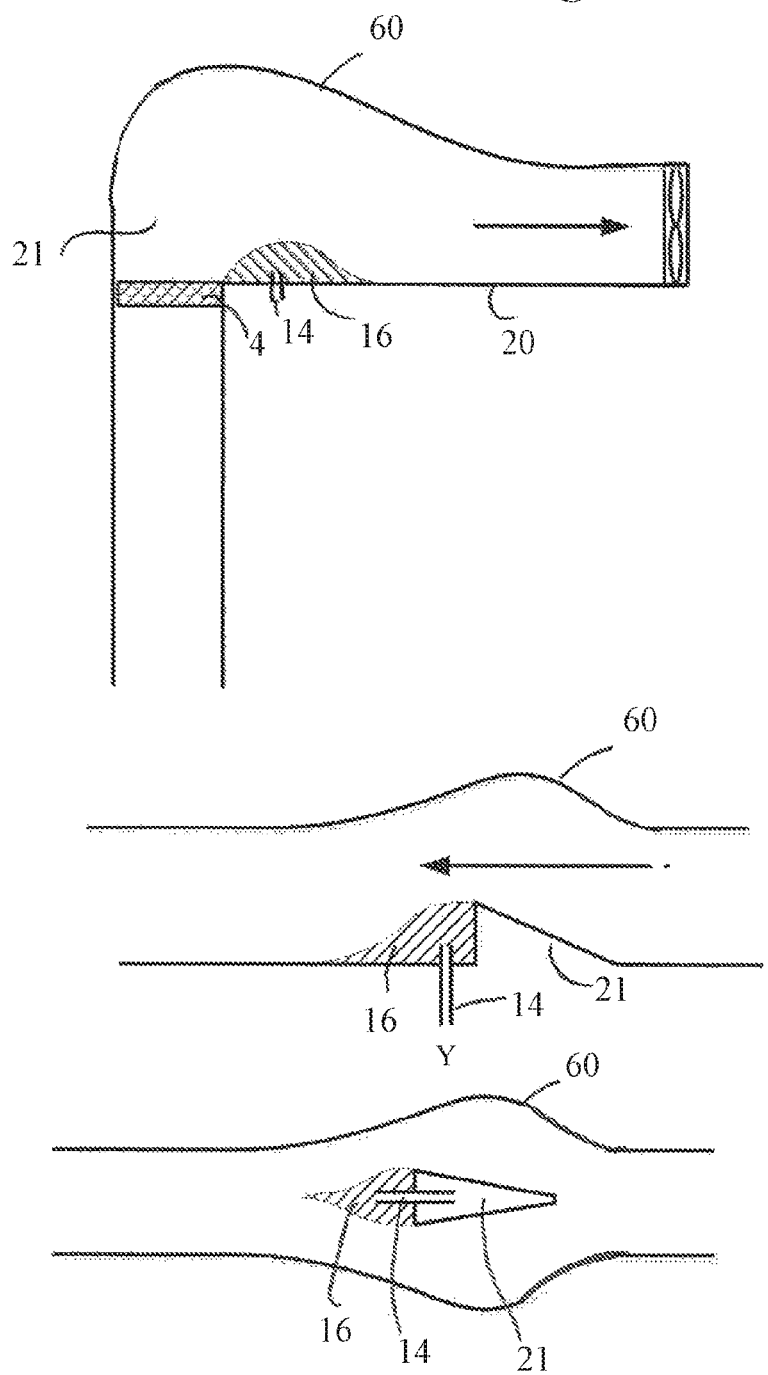
FIG. 7 illustrates possible modifications of the detector inlets shown in FIGS. 1 to 6.

FIG. 7 illustrates some embodiments of detector inlets in which the flow passage 20 comprises variations 60 in the shape and/or area of its cross section to accommodate changes in flow caused by the flow director 21. These variations 60 in cross section may be arranged at least partially downstream of the flow director 21, for example at least part of the variation 60 in cross section may be arranged downstream from the upstream end of the flow director 21. For example these variations in cross section may be configured to promote laminar flow of fluid past the flow director. In some embodiments the variations comprise a bulge in at least one wall of the flow passage. The bulge may comprise curved, sloped or graduated portions arranged to accommodate variations in fluid flow caused by the flow director.

The disclosure above has made reference to particular types of apparatus, but features of the embodiments described may be substituted for functionally equivalent elements. For example, the controller 12 of the apparatus may be provided by any appropriate processing means such as an FPGA, an ASIC, a general purpose processor, or an appropriate arrangement of logic gates. In addition, the flow provider 18 may comprise pump or a fan or any other device capable of inhaling a flow of fluid along the flow passage. As another example, the heater 4 described with reference to FIG. 1 may be arranged in any of the other detector inlets described above to heat the flow of fluid upstream from the sampling inlet 14. Such heaters 4 may comprise a resistive heater, such as a tape or membrane heater, or it may be provided by a source of radiative heat such as an infrared light source, for example a laser. In some examples the heater may comprise a jet of heated air. Particular examples of analytical apparatus have been described, such as mass spectrometers and ion mobility spectrometers, but other kinds of analytical apparatus may also be used. Other examples and variations will be apparent to the skilled addressee in the context of the present disclosure. It will also be apparent that features of each of the embodiments described with reference to each of the drawings may be combined, individually or otherwise, with some or all or the features of any of the other embodiments. Method features may be implemented by suitably configured apparatus, and the methods of operation described with reference to particular types of apparatus are intended as an independent disclosure of the methods themselves

The invention claimed is:

1. A detector comprising:
    an analytical apparatus for detecting a substance of interest;
    a detector inlet, the detector inlet comprising:
        a flow passage for carrying a flow of fluid along a flow path from an upstream end of the flow passage to a downstream end of the flow passage, the flow passage comprising a sampling volume occupying a subset of a width of the flow passage;
        a sampling inlet positioned adjacent the sampling volume and adapted to collect samples of the fluid from the sampling volume as the fluid flows past the sampling inlet in the subset of the width of the flow passage, and to provide the samples to the analytical apparatus, wherein the flow of fluid carries particulates; and
        a flow director positioned along the flow path upstream of the sampling inlet and arranged to vary a spatial distribution of the particulates carried by the fluid to increase a relative proportion of the particulates carried past the sampling inlet along the flow passage without entering the sampling volume, wherein the sampling inlet comprises at least one of: a pinhole inlet, a membrane inlet, or a capillary inlet;
        a flow provider positioned along the flow path downstream of the sampling inlet and the flow director that directs the flow of fluid past the flow director and the sampling inlet; and
        a controller adapted to control a sampler to collect samples of the fluid from the sampling volume through the sampling inlet and to provide the samples to the analytical apparatus.

2. The detector of claim 1, wherein the flow director is arranged to vary the distribution by accelerating part of the flow of fluid.

3. The detector of claim 2, wherein accelerating comprises changing the direction of the flow.

4. The detector of claim 1, wherein the flow director is arranged so that a speed of part of the flow of fluid past the sampling volume along the flow passage is greater than the speed of flow of fluid upstream from the sampling volume.

5. The detector of claim 1, wherein the flow director is provided by a change in direction of the flow passage.

6. The detector of claim 1, wherein the flow director comprises a variation in cross section of the flow passage.

7. The detector of claim 6, wherein the flow director comprises a reduction in the cross section of the flow passage.

8. The detector inlet of claim 6, wherein the flow director comprises an increase in cross section of the flow passage to provide a recess, and the sampling inlet is arranged in the recess.

9. The detector of claim 1, further comprising a sampler coupled to the sampling inlet and configured to draw a selected volume of fluid out of the sampling volume through the sampling inlet, wherein the selected volume of fluid is smaller than the sampling volume.

10. The detector of claim 1, further comprising a heater for heating the flow of fluid.

11. The detector of claim 10, wherein the heater is arranged to heat the flow of fluid upstream from the sampling inlet.

12. The detector of claim 1, wherein the analytical apparatus comprises at least one of a spectrometer or a chromatography apparatus.

13. The detector of claim 1, wherein the sampling inlet comprises a pinhole inlet.

14. The detector of claim 1 configured to detect a substance of interest in a sample of vapour obtained from a flow of fluid carrying particulates, utilizing a method comprising: directing the flow of fluid past the sampling inlet; varying the shape of a distribution of particulates, transverse to the direction of flow, relative to the shape of said distribution upstream of the sampling inlet, so that the particulates carried by the flow are inhibited from flowing through the sampling volume around the sampling inlet; obtaining at least one sample from the sampling volume via the sampling inlet; and providing the sample to the analytical apparatus to detect the substance of interest.

15. The method of claim 14, further comprising changing the direction of the flow upstream of the sampling inlet to reduce a probability that particulates carried past the sampling inlet by the flow will enter the sampling volume.

16. The method of claim 14, wherein the volume of the obtained sample is selected to be smaller than the sampling volume.

17. The method of claim 16, further comprising obtaining a plurality of said samples, wherein the rate at which the samples are obtained is selected based on the volume of said sample, and the rate at which vapour passes into the sampling volume from the flow of fluid.

18. The method of claim 14, further comprising heating the flow of fluid upstream from the sampling inlet to vapourise at least some of the particulates.

19. The method of claim 14, wherein the analytical apparatus comprises at least one of a spectrometer or a chromatography apparatus.

20. A detector comprising:
    an analytical apparatus for detecting a substance of interest, and
    a detector inlet, the detector inlet comprising:
        a flow passage for carrying a flow of fluid, the flow passage comprising a sampling volume;
        a sampling inlet adapted to collect samples of the fluid from the sampling volume as the fluid flows past the sampling inlet, and to provide the samples to the analytical apparatus, wherein the flow of fluid carries particulates; and
        a flow director arranged to vary a spatial distribution of the particulates carried by the fluid to increase a relative proportion of the particulates carried past the sampling inlet along the flow passage without entering the sampling volume, wherein the sampling inlet comprises at least one of: a pinhole inlet, a membrane inlet, or a capillary inlet;
    a flow provider that directs the flow of fluid past the flow director and the sampling inlet; and
    a controller adapted to control a sampler to collect samples of the fluid from the sampling volume through the sampling inlet and to provide the samples to the analytical apparatus, wherein at least one of the shape or area of a cross section of the flow passage is modified downstream of the flow director to accommodate changes in the flow of fluid caused by the flow director.

* * * * *